United States Patent [19]
Kaneko et al.

[11] 4,367,289
[45] Jan. 4, 1983

[54] METHOD OF PRODUCING COENZYME $Q_{10}$

[75] Inventors: Yasuyuki Kaneko, Nagoya; Masao Itoh, Anjyo; Shinji Takahashi, Nagoya; Masako Iritani, Chiryu, all of Japan

[73] Assignee: Nagoya University, Nagoya, Japan

[21] Appl. No.: 305,809

[22] Filed: Sep. 25, 1981

[30] Foreign Application Priority Data

Oct. 7, 1980 [JP] Japan ................................ 55/139249

[51] Int. Cl.$^3$ .......................... C12P 7/66; C12R 1/645
[52] U.S. Cl. ..................................... 435/133; 435/911
[58] Field of Search ........................................ 435/133

[56] References Cited

U.S. PATENT DOCUMENTS

| 3,769,170 | 10/1973 | Kondo et al. | 435/133 |
| 4,070,244 | 1/1978 | Nakao et al. | 435/133 |
| 4,205,125 | 5/1980 | Aida et al. | 435/133 |
| 4,220,719 | 9/1980 | Aida et al. | 435/133 |
| 4,245,048 | 1/1981 | Hata et al. | 435/133 |

FOREIGN PATENT DOCUMENTS 47-20396 6/1972 Japan .

Primary Examiner—Lionel M. Shapiro
Attorney, Agent, or Firm—Ladas & Parry

[57] ABSTRACT

Coenzyme $Q_{10}$ which is useful as a raw material of medicines for curing various diseases such as heart diseases, hypertension, etc. can economically be mass produced in a culture medium containing an extremely large quantity of p-hydroxybenzoic acid by using Rhodotorula sp. No. 46a strain.

14 Claims, 2 Drawing Figures

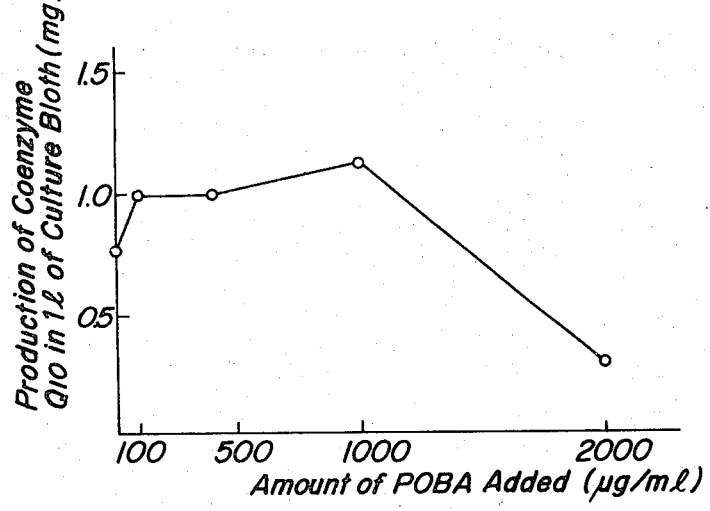
FIG_1
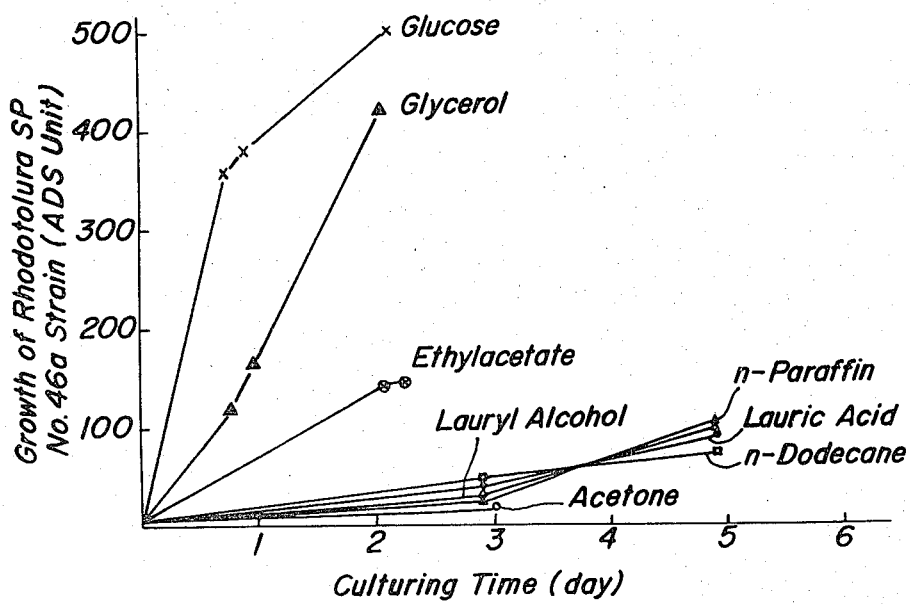
FIG_2

METHOD OF PRODUCING COENZYME $Q_{10}$

BACKGROUND OF THE INVENTION

The present invention relates to a method of producing coenzyme $Q_{10}$.

Recently, coenzyme $Q_{10}$ (abbreviated as $CoQ_{10}$) has been interested as a raw material for medicines for curing various diseases such as heart diseases, hypertension, tumor, etc. and can be produced by various microorganisms. For example, journal of Fermentation Technology, 47, p. 553 (1969) discloses a method of improving productivity of coenzyme Q by adding as a component of culture medium p-hydroxybenzoic acid (abbreviated as POBA) which is a precursor in a biosynthetic pathway of coenzyme $Q_{10}$. However, the method has a defect that the produced coenzyme Q is $Q_9$ and not $Q_{10}$. Coenzyme $Q_9$ is substantially inactive to human body and hence it does not exhibit the aforementioned desired pharmaceutical effects.

Japanese Patent Application Publication No. 20,396/72 describes a method of producing $CoQ_{10}$ by culturing a yeast, genus Candida capable of producing coenzyme Q in a culture medium containing n-alkane and POBA or POBA and acetic acid or its salt. However, the method has a drawback that production of $CoQ_{10}$ is limited owing to the feature of using a yeast, genus Candida and to a fact that POBA has generally such a strong bactericidal property to microorganisms that can be used as a food-preservative so that its addition is restricted to 30 mg/l at the most. Therefore, the method has not been a practical industrial method of producing $CoQ_{10}$ because a yield of $CoQ_{10}$ is still considerably low.

Japanese Patent Application Laid-Open No. 89,086/79 describes a method of producing $CoQ_{10}$ by culturing in a culture medium a microorganism capable of producing $CoQ_{10}$. However, the method is useful practically only when the microorganism is *Paracoccus denitrificance* ATCC 19367 Strain, *Agrobacterium tsumefaciene* ATCC 4452 strain or *Rhodotolura rubra* ATCC 20258 strain.

Japanese Patent Application No. 65,739/80 and corresponding U.S. application Ser. No. 258,502 and EPC Patent Application No. 81302196.1 invented by Kaneko and Itoh of the inventors of the present application describe a method of producing $CoQ_{10}$ by culturing in a culture medium a microorganism capable of producing $CoQ_{10}$. However, the method is useful practically only when the microorganism is *Aureobasidium sp.* No. 14 strain (International deposition No. FERM BP-1) or *Trichosporon sp.* WY2-2 (International desposition No. FERM BP-2).

SUMMARY OF THE INVENTION

An object of the present invention is to provide a method of producing $CoQ_{10}$ in high yield in a culture medium containing a large quantity of POBA.

Another object of the present invention is to provide a method of producing $CoQ_{10}$ quickly in a culture medium containing a large quantity of POBA.

Still another object of the present invention is to provide a method of mass-producing $CoQ_{10}$ in a simple and economical industrial process in a culture medium containing a large quantity of POBA.

To achieve the above objects, the present invention provides a method of producing $CoQ_{10}$ wherein $CoQ_{10}$ is produced by culturing *Rhodotorula sp.* No. 46a strain (abbreviated as No. 46a strain) in a culture medium containing a large quantity of POBA. According to the method of the present invention, the culture medium can also contain ethanol as a main carbon source in addition to POBA.

BRIEF DESCRIPTION OF THE DRAWINGS

FIG. 1 is a characteristic graph showing a relation between concentration of POBA added and production of $CoQ_{10}$ in 1 l of culture medium; and FIG. 2 is a characteristic graph showing influences of various main carbon sources upon growth rate of No. 46a strain.

DETAILED EXPLANATION OF THE INVENTION

We have made various experiments and studies on relations between nutrient culture media and microorganisms capable of producing $CoQ_{10}$, particularly of No. 46a strain, leading to a finding that No. 46a strain does not die even when POBA is added in such an amount that exceeds far beyond generally used. To the contrary, the productivity of $CoQ_{10}$ is increased. It is quite surprising that No. 46a strain can be tolerant to a high concentration of POBA, makes growth and produces $CoQ_{10}$ in exceedingly high yield.

Accordingly, in an aspect of the present invention, the present invention produces $CoQ_{10}$ by culturing No. 46a strain in a culture medium wherein a large quantity of POBA is added to high concentration.

No. 46a strain is the microorganism which we deposited to Fermentation Research Institute (Fermenation Research Institute, Agency of Industrial Sience and Technology, Ministry of International Trade and Industry) (abbreviated as FRI) on May 26, 1980 with Deposite No. 5,544 (International Deposition No. FERM BP-52).

The characteristics of *Rhodotorula sp.* No. 46a strain are as follows.

(1) Morphological and cultural characteristics
  1. Growth in malt extract
      After 24 hours at 30° C., cells are short-oval to elliptical, single or in pairs, $(2.6-2.8) \times (3.6-6)\mu$.
      Vegetative reproduction by budding.
      After 10 days at 25° C., there is yellowish-pink ring and sediment.
  2. Streak culture on malt agar
      After 3 days at 30° C., abundant growth along the inoculated streak, pink or yellowish-pink, smooth, dull, translucent and mucoid with entire margine.
  3. Slide culture, potato agar
      True mycelium, pseudomycelium, chlamydospore and arthrospore are not observed.
  4. Streak culture on Gorodkowa agar
      Ascospore and ballistospore are not observed.
  5. Giant colony on malt gelatin
      After 14 days at 30° C., yellowish-pink, mucoid and dull. Pseudomycelium absent.

(2) Physiological properties
  1. Optimum condition for growth: pH 6, 30° C.
  2. Range of condition for growth: pH 3-9, 15°-37° C.
  3. Relation to free oxygen: aerobic
  4. Assimilation of $KNO_3$: negative
  5. Action in BCP milk: unchanged
  6. Liquefaction of gelatin: negative
  7. Growth in vitamin-free medium: inducibly positive 8. Production of carotenoid pigments: positive
9. Splitting arbutin: positive
10. Production of starch-like compounds: negative
11. Fat splitting: negative
12. Utilization of nitrogen sources:
    Peptone and $(NH_4)_2SO_4$ are utilized.
13. Utilization of carbon sources:
    Glucose, D-mannose, galactose, fructose, sucrose, maltose, trehalose, D-xylose, D-arabinose, L-arabinose, D-ribose, melezitose, cellobiose, D-mannitol, lactic acid, succinic acid, citric acid, ethanol and grycerol are utilized. Acids are produced from glucose, galactose, maltose and sucrose, but those are not fermented. Lactose, raffinose, α-methyl-glucoside, soluble starch, inulin, melibiose, L-rhamnose, dulcitol, D-sorbitol, i-inositol are not utilized.

Considering the foregoing characteristics, the No. 46a strain was identified as relating strain to *Rhodotorula marina* according to "The yeasts, a taxonomic study" (1970) edited by J. Lodder.

We have also found that POBA is preferably added in a concentration of about 100–1,500 μg/ml to a culture medium at a temperature of about 20°–37° C. when No. 46a strain is used. If the concentration is less than about 100 μg/ml, the effect of addition cannot be exhibited sufficiently for increasing the production of $CoQ_{10}$, while if the concentration is larger than about 1,500 μg/ml, the bactericidal property of POBA is exhibited so much and the growth is suppressed so that the growth rate decreases. A concentration of about 800–1,200 μg/ml is particularly preferable.

According to the present invention, any carbon source can be used as far as No. 46a strain of the present invention can assimilate. For instance, carbohydrates such as starch, corn starch, etc.; alcohols such as glycerol, propanol, etc.; sugars such as glucose, sucrose, molasses, etc.; hydrocarbons such as aliphatic and aromatic hydrocarbons; or organic acids such as plamitic acid, fumalic acid, etc. can be used.

We have found out also that coenzyme $Q_{10}$ can be produced not only in extremely short period of time but also in exceedingly high yield, if ethanol is used as a carbon source in addition to POBA.

Accordingly, in another aspect of the present invention, the method of the present invention produces $CoQ_{10}$ by culturing No. 46a strain in a culture medium containing ethanol as a main carbon source in addition to a large quantity of POBA.

The quantity of ethanol to be added is about 0.5–4.0% (V/V) to the culture medium. If the quantity is less than about 0.5% (V/V), the amount of the cells produced becomes less. If the concentration is larger than about 4.0% (V/V), the bactericidal property of ethanol is exhibited so much and the growth is suppressed to decrease the growth rate. A quantity of about 1.0–3.0% (V/V) is particularly preferable.

In the present invention, usual nitrogen sources, vitamines, inorganic salts, etc. generally used can be added in usual amounts to the culture medium.

Preferable culturing conditions are a pH of about 3–8, a temperature of about 20°–37° C., a culturing period of about 20–80 hrs. and an aerobic atmosphere.

If pH value varies noticeably during culturing process to suppress the growth of the cells, pH is preferably adjusted by addition of an acidic or alkaline material.

DESCRIPTION OF THE PREFERRED EMBODIMENTS

Hereinafter, the preset invention will be explained in more detail with reference to preferred embodiments which however should not be construed by any means as limitations of the scope of the present invention.

In the succeeding examples, all quantities of materials are shown by gram unit, unless otherwise specified.

EXAMPLE 1

In this Example, $CoQ_{10}$ is produced using No. 46a strain.

Inoculum cells are cultured in a MPY medium which has the following composition.

Composition of the MPY medium:

| Malt extract broth | 30 |
|---|---|
| Peptone | 5 |
| Yeast extract | 0.1 |
| Tap water | 1 l |

The culture medium used for pre-culture and main culture has the following composition.

Composition of culture medium used for pre-culture and main culture:

| $NH_4NO_3$ | 5.0 |
|---|---|
| $KH_2PO_4$ | 2.5 |
| $MgSO_4.7H_2O$ | 1.0 |
| NaCl | 0.1 |
| Yeast extract | 0.1 |
| $CaCl_2.2H_2O$ | 0.01 |
| $FeCl_3.6H_2O$ | 0.01 |
| $C_2H_5OH$ | 20 ml |
| POBA | 0 (pre-culture) |
|  | 0–2,000 μg/ml |
|  | (main culture) |
| Tap water | 980 ml |
| pH | 5.0 |

Culturings are effected as follows.

A loopful cells from a young slant culture is inoculated to 10 ml of the MPY medium, and cultured at 30° C. for 7 days to obtain inoculum cell suspension.

A drop of the inoculum cell suspension is inoculated to 100 ml of the above-mentioned pre-culture medium not containing POBA and subsequently subjected to shaking culture at 30° C. for 48 hrs. to yield a pre-culture broth.

The pre-culture broth is added to 900 ml of the aforementioned main culture medium containing POBA in a concentration of 0–2,000 μg/ml in a volume ratio of 1:9 to give a total volume of 1 l and subjected again to shaking culture at 30° C. for 48 hrs. to yield a culture broth containing a large amount of grown cells.

The grown cells are separated by centrifugal precipitation of the culture broth and washed three times with distilled water. Suspension of wet cells thus obtained are treated in the following procedure to give a raw sample for extracting coenzyme $Q_{10}$.

Extracting method is as follows.

The mixture of 50 ml of the suspension of the wet cells, 150 ml of methanol, 5 g of pyrogallol and 20 g of sodium hydroxide are subjected to saponification by treating under a reflux condenser at 90° C. for 1 hr. and subsequently quickly cooled and thereafter extracted twice with each 100 ml of n-hexane. The n-hexane layer of total 200 ml is washed three times with distilled water, then dehydrated and dried overnight with anhydrous sodium sulfate, and thereafter concentrated under reduced pressure. The sample thus obtained is used for the quantitative analysis of $CoQ_{10}$ in the following way.

The concentrate is dissolved in 7 ml of ethanol to yield a sample solution.

Two ml of the sample solution, 0.5 ml of ethylcyanoacetate (ECA) and 0.5 ml of 0.2 N-KOH aqueous solution are mixed. After exactly 10 min., Optical Density at 625 nm ($OD_{625}$) is determined. As a control, $OD_{625}$ is determined for a similar mixed solution wherein instead of ECA an equal amount of ethanol is used and reacted in the same way. The control value is subtracted from the above determined value. The results are shown in Table 1.

TABLE 1

(Analytical results)

| POBA concentration ($\mu$g/ml) | $Q_{10}$ production (mg) / 1 l culture broth |
|---|---|
| 0 | 0.77 |
| 100 | 0.91 |
| 500 | 0.91 |
| 1,000 | 1.12 |
| 2,000 | 0.28 |

The above results are also shown as a characteristic graph in the attached FIG. 1.

EXAMPLE 2

In this Example, growth of cells of No. 46a strain are observed on various pre-culture media containing instead of ethanol various types of main carbon source of which No. 46a strain can assimilate.

Main carbon sources used are glucose, glycerol, ethylacetate, acetone, n-propanol, a mixture of n-paraffins, n-dodecane, lauric acid and lauryl alcohol.

Culturing is effected as follows.

A loopful of cells from a young slant culture is inoculated to 10 ml of the MPY medium, and cultured at 30° C. for 7 days to obtain inoculum cells.

A drop of the inoculum cell suspension is inoculated to the same media as pre-culture media except that it is not containing POBA and each containing one of the aforementioned main carbon sources instead of ethanol and subsequently subjected to shaking culture at 30° C.

When a main carbon source which is not soluble in water is used in the medium, a detergent Tween 80 (a commercially available surfactant, polyoxyethyl, sorbitan monooleate, from Kao-Atlas Chemicals Co., Ltd. Japan) is added in an amount of 0.5 g/l for assisting the dissolution of the water-insoluble main carbon source.

Growth of No. 46a strain in the various media are determined at various culturing time. The results are shown in Table 2.

TABLE 2

(Growth of No. 46a strain in ADS unit)

| Main Carbon Source | Culturing Time (day) | | | | | | |
|---|---|---|---|---|---|---|---|
| | 0.75 | 1.0 | 2.0 | 2.25 | 2.9 | 3.0 | 4.9 |
| Acetone | — | — | — | — | — | 12 | — |
| n-Dodecane | — | — | — | — | 50 | — | 95 |
| Lauric Acid | — | — | — | — | 40 | — | 80 |
| n-Paraffins | — | — | — | — | 20 | — | 102 |
| Lauryl Alcohol | — | — | — | — | 30 | — | 90 |
| Ethyl Acetate | — | — | 80 | 85 | — | — | — |
| Glycerol | 128 | 175 | 420 | — | — | — | — |
| Glucose | 360 | 380 | 502 | — | — | — | — |

Note:
130 of ADS unit is nearly equivalent to 1.0 of OD 660 unit.

The above results are also shown as a characteristic graph in the attached FIG. 2.

EXAMPLE 3

In this Example, two experiments are conducted wherein No. 46a strain is grown in various main culture media wherein POBA is added in a high concentration to produce $CoQ_{10}$. Amount of main carbon source used is, 20 g of glucose, 20 ml of glycerol or 30 ml of ethanol per 1 l of pre-culture medium for experiment 1, and 20 ml of ethanol or 20 g of sodium acetate for experiment 2. Amount of POBA added is 1,000 $\mu$g/ml in both experiments 1 and 2.

Culturings are effected as follows.

An inoculum cell suspension is prepared in the same manner as in Example 1.

A drop of the inoculum cell suspension is inoculated to each 200 ml of the pre-culture media not containing POBA and containing the aforementioned amount of main carbon source instead of ethanol subsequently subjected to shaking culture at 30° C. for 48 hrs. to yield pre-culture broths.

Fifty ml of the pre-culture broth is added to 450 ml of the main culture medium containing POBA in a concentration of 1,000 $\mu$g/ml in a volume ratio of 1:9 to give a total volume of 500 ml and subjected again to shaking culture at 30° C. for 48 hrs. to yield a culture broth containing a large amount of grown cells.

The grown cells are separated by centrifugal precipitation of the culture broth and washed three times with distilled water. Suspension of wet cells thus obtained is treated in the same procedure as in Example 1 to give a raw sample for extracting coenzyme $Q_{10}$.

$CoQ_{10}$ in the raw sample is determined in the same manner as in Example 1 for experiment 1, while it is determined by a high performance liquid chromatography for experiment 2. The results are shown in Table 3.

TABLE 3

(Analytical results)

| Experiment | Main Carbon Source | Amount of Produced $CoQ_{10}$ (mg) / 1 l culture broth | Amount of Produced $CoQ_{10}$ ($\mu$g) / 1 g wet cells |
|---|---|---|---|
| 1 | Glucose 2% | 0.56 | 56.1 |
| | Glycerol 2% | 0.70 | 76 |
| | Ethanol 3% | 1.26 | 265 |
| 2 | Ethanol 2% | 2.90 | 1700 |
| | Sodium Acetate 2% | 2.15 | 1370 |

The high performance liquid chromatography used in experiment 2 is Hitachi 635 type apparatus equipped with column No. 3,055. The apparatus is used under a pressure of 40 kg/cm², an absolute methanol flow rate is 0.7 ml/min and a measuring light wave length UV 280 nm, a full scale OD 0.64. Measured values are converted to the quantitative analytical values by comparing them with a standard curve preliminarily prepared for known values.

As clearly indicated from the above analytical results, the present invention is exceedingly superior to conventional methods.

Although the present invention has been explained in detail with specific values and embodiments, it will of course be apparent to those skilled in the art that many variations and modifications are possible without departing from the broad aspect and scope of the present invention as defined in the appended claims.

What is claimed is:

1. A method of producing coenzyme $Q_{10}$, comprising, culturing a microorganism of *Rhodotorula sp.* No. 46a strain in a culture medium containing a large quantity of p-hydroxybenzoic acid to produce coenzyme $Q_{10}$.

2. A method as defined in claim 1, wherein the microorganism of *Rhodotorula sp.* No. 46a strain in the culture medium containing p-hydroxybenzoic acid in a concentration of about 100–1,500 µg/ml at a temperature of about 20°–37° C.

3. A method as defined in claim 2, wherein the concentration of p-hydroxybenzoic acid is about 800–1,200 µg/ml.

4. A method as defined in claim 1, wherein the culturing is effected at a pH value of about 3–8.

5. A method as defined in claim 1, wherein the culturing is effected in an aerobic atmosphere for about 20–80 hrs.

6. A method as defined in claim 1, wherein the culture medium is added with a material selected from the group consisting of acidic material and alkaline material during the cultivation.

7. A method of producing coenzyme $Q_{10}$, comprising, culturing a microorganism of *Rhodotorula sp.* No. 46a strain in a culture medium containing a large quantity of p-hydroxybenzoic acid to which ethanol is added as a main carbon source to produce coenzyme $Q_{10}$.

8. A method as defined in claim 7, wherein the microorganism of *Rhodotorula sp.* No. 46a strain is cultured in the culture medium containing p-hydroxybenzoic acid in a concentration of about 100–1,500 µg/ml at a temperature of about 20°–37° C.

9. A method as defined in claim 8, wherein the concentration of p-hydroxybenzoic acid is about 800–1,200 µg/ml.

10. A method as defined in claim 7, wherein ethanol is added to the culture medium in a concentration of about 0.5–4.0% (V/V).

11. A method as defined in claim 10, wherein ethanol is added to the culture medium in a concentration of about 1.0–3.0% (V/V).

12. A method as defined in claim 7, wherein the culturing is effected at a pH value of about 3–8.

13. A method as defined in claim 7, wherein the culturing is effected in an aerobic atmosphere for about 20–80 hrs.

14. A method as defined in claim 7, wherein the culture medium is added with a material selected from the group consisting of acidic material and alkaline material during the cultivation.

* * * * *